United States Patent [19]

Shutske

[11] Patent Number: 5,013,741

[45] Date of Patent: May 7, 1991

[54] N-[SUBSTITUTED ALKYLIDENE]-1,2,3,4-TETRAHYDRO-9-ACRIDINAMINES USEFUL FOR ENHANCING THE CHOLINERGIC FUNCTION IN A MAMMAL

[75] Inventor: Gregory M. Shutske, Somerset, N.J.

[73] Assignee: Hoechst-Roussel Pharmaceuticals Incorporated, Somerville, N.J.

[21] Appl. No.: 223,846

[22] Filed: Jul. 25, 1988

Related U.S. Application Data

[63] Continuation-in-part of Ser. No. 93,935, Sep. 8, 1987, abandoned.

[51] Int. Cl.$^5$ ............... C07D 219/10; C07D 221/16; A61K 31/47
[52] U.S. Cl. ................................ 514/290; 514/297; 546/79; 546/93; 546/105; 546/107
[58] Field of Search ............... 546/79, 93, 105, 106, 546/107; 514/290, 297

[56] References Cited

U.S. PATENT DOCUMENTS

| | | | |
|---|---|---|---|
| 3,232,945 | 2/1966 | Signal, Jr. et al. | 546/93 |
| 3,318,895 | 5/1967 | Pribyl et al. | 546/93 |
| 3,318,896 | 5/1967 | Pribyl et al. | 546/93 X |
| 3,541,066 | 11/1970 | Wolf | 546/63 |
| 3,580,915 | 5/1971 | Wolf et al. | 546/63 |
| 3,637,706 | 1/1972 | Wolf et al. | 544/361 |
| 3,647,800 | 3/1972 | Wolf et al. | 546/81 |
| 3,657,233 | 4/1972 | Wolf et al. | 544/127 |
| 3,674,790 | 7/1972 | Wolf et al. | 546/81 |
| 3,987,047 | 10/1976 | Griss et al. | 540/580 |
| 4,108,998 | 8/1978 | Demerson et al. | 514/291 |
| 4,631,286 | 12/1986 | Shutske et al. | 514/297 |
| 4,695,573 | 9/1987 | Shutske et al. | 514/290 |
| 4,762,841 | 8/1988 | Shutske | 514/278 |
| 4,816,456 | 3/1989 | Summers | 514/255 |
| 4,851,536 | 7/1989 | Skotnicki et al. | 546/106 |
| 4,985,430 | 1/1991 | Morita et al. | 514/253 |

FOREIGN PATENT DOCUMENTS

| | | |
|---|---|---|
| 0165592 | 12/1985 | European Pat. Off. |
| 0179383 | 4/1986 | European Pat. Off. |
| 0268871 | 6/1988 | European Pat. Off. |
| 1022940 | 3/1966 | United Kingdom ............ 546/79 |
| WO89/02739 | 4/1989 | World Int. Prop. O. |
| WO89/02740 | 4/1989 | World Int. Prop. O. |

OTHER PUBLICATIONS

Abramochkin et al., Khim.-Farm. Zh. (English Language Version), vol. 4(7), pp. 10-13 (1970).
Konshin et al. (I), Khim.-Farm. Zh. (English Language Version), vol. 5(11), pp. 10-12 (1971).
Konshin et al. (II), Izv. Vyssh. Ucheb. Zaved. Khim. Khim. Tekhnol. (English Language Version), vol. 15(2), pp. 243-244 (1972).
Konshin et al. (III), Izv. Vyssh. Ucheb. Zaved. Khim. Khim. Tekhnol. (English Language Version), vol. 15(5), pp. 726-727 (1972).
Konshin et al. (IV), Khim. Geterotsikl. Soedin. (English Language Version), 1973 (No. 4), pp. 531-534.
Konshin et al. (V), Khim.-Farm. Zh. (English Language Version), vol. 8(7), pp. 17-19 (1974).
Konshin, Nauch. Tr. Perm. Farmstsevt. Int. (English Language Version), vol. 10, pp. 6-9 (1976).
Khaldeeva et al., Khim. Getrotsikl. Soedin. (English Language Translation), 1976, No. 2, pp. 263-265.
Bialevsky, Coll. Czech. Chem. Commun., vol. 42, pp. 2802-2808 (1977).
Krisna et al., Ind. J. Chem., vol. 16B(2), pp. 156-158 (1978).
Bun-Hoi et al., Chemical Abstracts, vol. 69: 106408d (1968).
Patnaik et al., J. Med. Chem., vol. 9, pp. 483-488 (1966).
Steinberg et al., J. Med. Chem., vol. 18(11), pp. 1056-1061 (1975).
Ferguson et al., Chemical Abstracts, vol. 98:154912j (1983).
Ferguson et al., Chemical Abstracts, vol. 102:73854r (1985).
Flood et al., Chemical Abstracts, vol. 103(7):48119t (1985).
Cherkin et al., Chemical Abstracts, vol. 100(5):114871y (1984).

*Primary Examiner*—Diana Rivers
*Attorney, Agent, or Firm*—Tatsuya Ikeda

[57] ABSTRACT

There are disclosed compounds having the formula wherein n is 1-4; $R_1$ is hydrogen, alkyl, aryl, aryllower-alkyl, naphthyl, furyl, thienyl, pyridinyl or pyrrolyl; X is hydrogen, loweralkyl, cycloalkyl, loweralkoxy, halogen, hydroxy nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; stereo, optical and geometrical isomers thereof, and pharmaceutically acceptable acid addition salts thereof, which are useful for enhancing memory and pharmaceutical compositions comprising an effective memory enhancing amount of such a compound.

67 Claims, No Drawings

N-[SUBSTITUTED ALKYLIDENE]-1,2,3,4-TETRAHYDRO-9-ACRIDINAMINES USEFUL FOR ENHANCING THE CHOLINERGIC FUNCTION IN A MAMMAL

This is a continuation-in-part of a co-pending prior application, Ser. No. 093,935, filed Sept. 8, 1987, now abandoned.

This invention relates to compounds having the formula

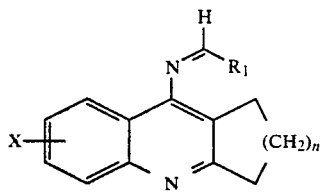

wherein n is 1–4; $R_1$ is hydrogen, alkyl, aryl, arylloweralkyl, naphthyl, furyl, thienyl, pyridinyl or pyrrolyl; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NH-COR$_2$ or —NR$_3$R$_4$ where $R_2$ is hydrogen or loweralkyl, and $R_3$ and $R_4$ are independently hydrogen, loweralkyl or cycloalkyl; stereo, optical and geometrical isomers thereof, and pharmaceutically acceptable acid addition salts thereof, which are useful for enhancing memory and pharmaceutical compositions comprising an effective memory enhancing amount of such a compound.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term alkyl denotes a straight or branched alkyl group having from 1 to 18 carbon atoms. Examples of said alkyl include methyl, n-propyl, iso-butyl, heptyl, decyl, dodecyl, hexadecyl and octadecyl.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term halogen shall mean fluorine, chlorine, or bromine or iodine.

Unless otherwise stated or indicated, the term aryl shall mean an unsubstituted phenyl group, a phenyl group substituted with 1, 2 or 3 substituents each of which being independently loweralkyl, loweralkoxy, halogen, hydroxy, trifluoromethyl, phenoxy or benzyloxy.

The compounds of this invention are prepared by utilizing the synthetic scheme described below.

Synthetic Scheme

Compounds of Formula I can be prepared by reacting a compound of formula II with an aldehyde of formula III where the definitions of n, X and $R_1$ are as given before. Typically, said reaction is conducted in a suitable solvent such as benzene, toluene or xylene at a temperature of about 80°–150° C. in the presence of a base such as piperidine, morpholine, diethylamine or diisopropylamine.

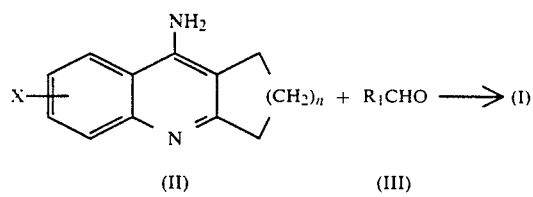

The compounds of Formula I of the present invention are useful in the treatment of various memory dysfunctions characterized by decreased cholinergic function, such as Alzheimer's disease.

This utility is manifested by the ability of these compounds to inhibit the enzyme acetyl cholinesterase and thereby increase acetylcholine levels in the brain. Further, the compounds of this invention are in general less toxic and have a broader therapeutic window than heretofore known compounds such as tacrine and physostigmine, making them more therapeutically acceptable.

The ability to inhibit acetylcholinesterase was determined by the photometric method of Ellman et al., Biochem. Pharmacol. 7, 88 (1961). Results of acetylcholinesterase inhibition for some of the compounds of this invention are presented in Table 1 along with those for reference compounds.

TABLE 1

| Acetylcholinesterase Inhibition Assay | |
|---|---|
| Compound | Acetylcholinesterase Inhibition IC$_{50}$ (molar) |
| N-Phenylmethylene-1,2,3,4-tetrahydro-9-acridinamine | 2.3 × 10$^{-7}$ |
| 9-Amino-N-[(2-hydroxyphenyl)methylene]-1,2,3,4-tetrahydroacridine, hemi-fumarate (Reference Compounds) | 5.1 × 10$^{-6}$ |
| Tacrine (9-amino-1,2,3,4-tetrahydroacridine) | 3.1 × 10$^{-7}$ |
| Physostigmine | 6.0 × 10$^{-9}$ |

This utility is further demonstrated by the ability of these compounds to restore cholinergically deficient memory in the Dark Avoidance Assay, where they are in general active over a broader dose range than heretofore known compounds, a distinct therapeutic advantage. In this assay mice are tested for their ability to remember an unpleasant stimulus for a period of 24 hours. A mouse is placed in a chamber that contains a dark compartment; a strong incadescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for a representative compound of this invention and reference compounds are presented in Table 2.

TABLE 2

Dark Avoidance Assay

| Compound | Dose (mg/kg of body weight, s.c) | % of Animals with Scopolamine Induced Memory Deficit Reversal |
| --- | --- | --- |
| N-Phenylmethylene-1,2,3,4-tetrahydro-9-acridinamine (Reference Compounds) | 0.31<br>5.0 | 27%<br>60% |
| Tacrine | 0.63 | 13% |
| Pilocarpine | 5.0 | 13% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:

N-(phenylmethylene)-1,2,3,4-tetrahydro-9-acridinamine;

N-[(4-fluorophenyl)methylene]-1,2,3,4-tetrahydro-9-acridinamine;

N-[(3-fluorophenyl)methylene]-1,2,3,4-tetrahydro-9-acridinamine;

N-[(2-fluorophenyl)methylene]-1,2,3,4-tetrahydro-9-acridinamine;

N-[(2-chlorophenyl)methylene]-1,2,3,4-tetrahydro-9-acridinamine;

N-[(4-chlorophenyl)methylene]-1,2,3,4-tetrahydro-9-acridinamine;

N-[(2,4-dichlorophenyl)methylene]-1,2,3,4-tetrahydro-9-acridinamine;

N-[(4-methoxyphenyl)methylene]-1,2,3,4-tetrahydro-9-acridinamine;

N-[(2-thienyl)methylene]-1,2,3,4-tetrahydro-9-acridinamine;

N-[(2-furyl)methylene]-1,2,3,4-tetrahydro-9-acridinamine;

6-chloro-N-(phenylmethylene)-1,2,3,4-tetrahydro-9-acridinamine;

7-chloro-N-(phenylmethylene)-1,2,3,4-tetrahydro-9-acridinamine;

7-methyl-N-(phenylmethylene)-1,2,3,4-tetrahydro-9-acridinamine;

7-methoxy-N-(phenylmethylene)-1,2,3,4-tetrahydro-9-acridinamine;

N-(phenylmethylene)-6-trifluoromethyl-1,2,3,4-tetrahydro-9-acridinamine;

N-[(2-methylphenyl)methylene]-1,2,3,4-tetrahydro-9-acridinamine;

N-[(4-methylphenyl)methylene]-1,2,3,4-tetrahydro-9-acridinamine;

N-[(4-nitrophenyl)methylene]-1,2,3,4-tetrahydro-9-acridinamine;

N-[(4-cyanophenyl)methylene]-1,2,3,4-tetrahydro-9-acridinamine;
N-[(2-hydroxyphenyl)methylene]-1,2,3,4-tetrahydro-9-acridinamine;
N-[(4-hydroxyphenyl)methylene]-1,2,3,4-tetrahydro-9-acridinamine;
1,2,3,4-tetrahydro-N-[(4-trifluoromethylphenyl)methylene]-9-acridinamine;
N-[(2-pyridinyl)methylene]-1,2,3,4-tetrahydro-9-acridinamine;
N-[(3-pyridinyl)methylene]-1,2,3,4-tetrahydro-9-acridinamine;
N-[(4-pyridinyl)methylene]-1,2,3,4-tetrahydro-9-acridinamine;
6-methoxy-N-(phenylmethylene)-1,2,3,4-tetrahydro-9-acridinamine;
6-methyl-N-(phenylmethylene)-1,2,3,4-tetrahydro-9-acridinamine;
7-methyl-N-(phenylmethylene)-1,2,3,4-tetrahydro-9-acridinamine;
6-fluoro-N-(phenylmethylene)-1,2,3,4-tetrahydro-9-acridinamine;
N-[(1-naphthyl)methylene]-1,2,3,4-tetrahydro-9-acridinamine;
N-[(2-naphthyl)methylene]-1,2,3,4-tetrahydro-9-acridinamine;
N-ethylidene-1,2,3,4-tetrahydro-9-acridinamine;
N-propylidene-1,2,3,4-tetrahydro-9-acridinamine;
N-(2-methylpropylidene)-1,2,3,4-tetrahydro-9-acridinamine;
N-butylidene-1,2,3,4-tetrahydro-9-acridinamine;
N-pentylidene-1,2,3,4-tetrahydro-9-acridinamine;
N-hexylidene-1,2,3,4-tetrahydro-9-acridinamine;
N-(4-methylpentylidene)-1,2,3,4-tetrahydro-9-acridinamine;
N-[(cyclopropyl)methylene]-1,2,3,4-tetrahydro-9-acridinamine;
N-[(cyclopentyl)methylene]-1,2,3,4-tetrahydro-9-acridinamine;
N-[(cyclohexyl)methylene]-1,2,3,4-tetrahydro-9-acridinamine;
N-[(cycloheptyl)methylene]-1,2,3,4-tetrahydro-9-acridinamine;
N-octylidene-1,2,3,4-tetrahydro-9-acridinamine;
N-decylidene-1,2,3,4-tetrahydro-9-acridinamine;
N-dodecylidene-1,2,3,4-tetrahydro-9-acridinamine;
N-tetradecylidene-1,2,3,4-tetrahydro-9-acridinamine;
N-hexadecylidene-1,2,3,4-tetrahydro-9-acridinamine;
N-octadecylidene-1,2,3,4-tetrahydro-9-acridinamine;
2,3-dihydro-N-(phenylmethylene)-1H-cyclopenta[b]quinolin-9-amine; and
N-(phenylmethylene)-2,3,4,5-tetrahydro-1H-cyclohepta[b]quinolin-10-amine.

The following examples are presented in order to illustrate this invention.

EXAMPLE 1

N-Phenylmethylene-1,2,3,4-tetrahydro-9-acridinamine 1,2,3,4-Tetrahydro-9-acridinamine (4.0 g) was dissolved in 400 ml of warm toluene and then morpholine (3.5 g) and benzaldehyde[1] (2.65 g) were added and the reaction mixture was brought to reflux with a Dean-Stark water separator. After the solution was refluxed overnight an additional 2.65 g of benzaldehyde was added and reflux was continued an additional five (5) hours. At the end of this time the volatiles were removed under reduced pressure and the residue was purified by flash chromatography (EtOAc) to give 3.18 g of pure porduct after trituration with $Et_2O$. Analytically pure material was obtained by recrystallization from cyclohexane, m.p. 168°–169° C.

[1] The benzaldehyde was freshly washed with aqueous $K_2CO_3$ solution.

Analysis. Calculated for $C_{20}H_{18}N_2$: 83.88% C; 6.33% H; 9.78% N. Found: 83.99% C; 6.34% H; 9.64% N.

EXAMPLE 2

N-[(2-Methylphenyl)methylene]-1,2,3,4-tetrahydro-9-acridinamine 1,2,3,4-Tetrahydro-9-acridinamine (4.0 g) was suspended in 400 ml of toluene to which morpholine (3.5 g) and o-tolualdehyde (3.0 g) were successively added. The reaction mixture was refluxed overnight and then an additional 1.5 g of aldehyde was added. Reflux was continued for an additional six (6) hours and then the reaction mixture was concentrated and purified by flash chromatography ($CH_2Cl_2$, then 20% $EtOAc/CH_2Cl_2$). Fractions containing the pure product were concentrated and recrystallized from benzene/pentane to give 3.32 g of analytically pure product, m.p. 160°–162° C.

Analysis. Calculated for $C_{21}H_{20}N_2$: 83.96% C; 6.71% H; 9.33% N. Found: 83.77% C; 6.78% H; 9.24% N.

EXAMPLE 3

N-[(4-Fluorophenyl)methylene]-1,2,3,4-tetrahydro-9-acridinamine 1,2,3,4-Tetrahydro-9-acridinamine (4.0 g) was refluxed in 400 ml of toluene that contained 3.5 g of morpholine and 3.10 g of 4-fluorobenzaldehyde that had been freshly washed in $K_2CO_3$. The reaction mixture was refluxed over two (2) nights and then concentrated, purified by flash chromatography (20% $EtOAc/CH_2Cl_2$) and recrystallized from dichloromethane/pentane to give 2.20 g of analytically pure product, m.p. 161°–163° C.

Analysis. Calculated for $C_{20}H_{17}FN_2$: 78.91% C; 5.63% H; 9.20% N. Found: 79.06% C; 5.66% H; 9.19% N.

EXAMPLE 4

N-[(2-Chlorophenyl)methylene]-1,2,3,4-tetrahydro-9-acridinamine 1,2,3,4-Tetrahydro-9-acridinamine (4.0 g) was suspended in 400 ml of toluene to which morpholine (3.5 g) and 2-chlorobenzaldehyde (3.5 g) were successively added. The reaction mixture was refluxed overnight and then an additional 1.7 g of aldehyde was added. Reflux was continued for an additional sixteen (16) hours and then the reaction mixture was concentrated and purified by flash chromatography ($CH_2Cl_2$, then 20% $EtOAc/CH_2Cl_2$). Fractions containing the product were concentrated and recrystallized from $Et_2O$/pentane to give 2.10 g of analytically pure product, m.p. 165°–166° C.

Analysis. Calculated for $C_{20}H_{17}ClN_2$: 74.87% C; 5.34% H; 8.73% N. Found: 74.75% C; 5.34% H; 8.57% N.

EXAMPLE 5

N-[4-Chlorophenyl)methylene]-1,2,3,4-tetrahydro-9-acridinamine 1,2,3,4-Tetrahydro-9-acridinamine (4.0 g) was refluxed in 400 ml of toluene that contained 3.5 g of morpholine and 3.5 g of 4-chlorobenzaldehyde that had been freshly washed in $K_2CO_3$. The reaction mixture was refluxed over two (2) nights and then concentrated, purified by flash chromatography (20% EtOAc/CH$_2$Cl$_2$) and recrystallized from dichloromethane/pentane to give 1.95 g of analytically pure product, m.p. 169°–170° C.

Analysis. Calculated for C$_{20}$H$_{17}$ClN$_2$: 74.87% C; 5.34% H; 8.73% N. Found: 74.78% C; 5.37% H; 8.65% N.

EXAMPLE 6

N-[(2,6-Dichlorophenyl)methylene]-1,2,3,4-tetrahydro-9-acridinamine 1,2,3,4-Tetrahydro-9-acridinamine (3.23 g) was suspended in 400 ml of toluene to which morpholine (2.8 g) and 2,6-dichlorobenzaldehyde (3.5 g) were successively added. The reaction mixture was refluxed overnight and then an additional 1.7 g of aldehyde was added. Reflux was continued for an additional sixteen (16) hours and then the reaction mixture was concentrated and purified by flash chromatography (CH$_2$Cl$_2$, then 20% EtOAc/CH$_2$Cl$_2$). Fractions containing the product were concentrated and recrystallized from benzene/hexane to give 2.18 g of analytically pure product, m.p. 200°–202° C.

Analysis. Calculated for C$_{20}$H$_{16}$Cl$_2$N$_2$: 67.61% C; 4.54% H; 7.89% N. Found: 67.47% C; 4.47% H; 7.73% N.

EXAMPLE 7

N-[(4-Methoxyphenyl)methylene]-1,2,3,4-tetrahydro-9-acridinamine 1,2,3,4-Tetrahydro-9-acridinamine (4.0 g) was refluxed overnight in 400 ml of toluene containing 3.5 g of morpholine and 3.4 g of 4-methoxybenzaldehyde. At the end of this time, an additional 1.7 g of aldehyde was added and heating was continued for six (6) more hours. The reaction mixture was then concentrated and purified by flash chromatography (CH$_2$Cl$_2$, then 10% EtOAc/CH$_2$Cl$_2$). Fractions containing the product were concentrated and recrystallized from benzene/pentane to give 3.37 g of analytically pure material, m.p. 160°–162° C.

Analysis. Calculated for C$_{21}$H$_{20}$N$_2$O: 79.72% C; 6.37% H; 8.85% N. Found: 79.78% C; 6.43% H; 8.82% N.

EXAMPLE 8

N-[(4-Trifluoromethylphenyl)methylene]-1,2,3,4-tetrahydro-9-acridinamine 1,2,3,4-Tetrahydro-9-acridinamine (4.00 g) was refluxed for twenty-four (24) hours in 400 ml of toluene that contained morpholine (3.50 g) and 4-trifluoromethylbenzaldehyde (4.35 g). At this time, an additional 2.0 g of aldehyde was added and reflux was continued for another sixteen (16) hours. At the end of this time the reaction mixture was concentrated and the residue was purified by flash chromatography (CH$_2$Cl$_2$, then 20% EtOAc/CH$_2$Cl$_2$). Fractions containing the product were concentrated and recrystallized from benzene/pentane to give 3.46 g of analytically pure product, m.p. 203°–205° C.

Analysis. Calculated for C$_{21}$H$_{17}$F$_3$N$_2$: 71.18% C; 4.84% H; 7.90% N. Found: 71.57% C; 4.88% H; 7.94% N.

EXAMPLE 9

9-Amino-N-[(2-hydroxyphenyl)methylene]-1,2,3,4-tetrahydroacridine, hemi-fumarate A mixture of 1,2,3,4-Tetrahydro-9-acridinamine (4.1 g), salicylaldehyde (3.3 ml) and morpholine (3.6 ml) in 200 ml toluene was refluxed, with removal of water, for two (2) hours. The solvents were concentrated off and the compound was passed through a column of florisil (DCM) to give 2.7 g of yellow solid, m.p. 173°–183° C.

The fumaric acid addition salt was formed in isopropanol and recrystallized from isopropyl ether/methanol to give 1.2 g of yellow powder, m.p. 217°–219° C.

Analysis. Calculated for C$_{20}$H$_{18}$N$_2$O.0.5C$_4$H$_4$O$_4$: 73.31% C; 5.59% H; 7.77% N. Found: 73.03% C; 5.77% H; 7.76% N.

EXAMPLE 10

N-[(4-Nitrophenyl)methylene]-1,2,3,4-tetrahydro-9-acridinamine 1,2,3,4-Tetrahydro-9-acridinamine (4.0 g) was refluxed in 400 ml of toluene containing morpholine (3.5 g) and 4-nitrobenzaldehyde (3.78 g). After forty-eight (48) hours an additional 3.78 g of aldehyde was added and reflux was continued for an additional twenty-four (24) hours. At the end of this time the reaction mixture was concentrated and purified by flash chromatography. Fractions containing the product were concentrated and recrystallized from CH$_2$Cl$_2$/pentane to give 3.38 g of product, m.p. 237°–238° C.

Analysis. Calculated for C$_{20}$H$_{17}$N$_3$O$_2$: 72.49% C; 5.17% H; 12.68% N. Found: 72.60% C; 5.12% H; 12.44% N.

EXAMPLE 11

N-[(4-Cyanophenyl)methylene]-1,2,3,4-tetrahydro-9-acridinamine 1,2,3,4-Tetrahydro-9-acridinamine (3.2 g) was refluxed in 300 ml of toluene containing morpholine (2.8 g) and 4-cyanobenzaldehyde (2.60 g). After twenty-four (24) hours the reaction mixture was concentrated and purified by flash chromatography. Fractions containing the product were concentrated and recrytallized from CH$_2$Cl$_2$/pentane to give 2.30 g of product, m.p. 204°–205° C.

Analysis. Calculated for C$_{21}$H$_{17}$N$_3$: 81.00% C; 5.50% H; 13.49% N. Found: 81.00% C; 5.48% H; 13.53% N.

EXAMPLE 12

N-[(1-Naphthyl)methylene]-1,2,3,4-tetrahydro-9-acridinamine 1,2,3,4-Tetrahydro-9-acridinamine (4.0 g) was refluxed in 400 ml of toluene that contained 3.5 g of morpholine and 3.10 g of 1-naphthaldehyde. The reaction mixture was refluxed over two (2) nights and then concentrated and purified by flash chromatography (20% EtOAc/CH$_2$Cl$_2$) to give 2.30 g of analytically pure product after crystallization from benzene/pentane, m.p. 229°–231° C.

Analysis. Calculated for C$_{24}$H$_{20}$N$_2$: 85.70% C; 6.00% H; 8.30% N. Found: 85.59% C; 5.88% H; 8.35% N.

We claim:

1. A compound of the formula

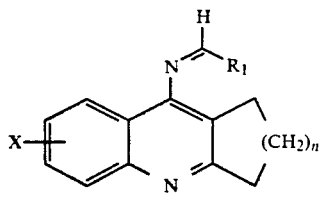

wherein n is 1–4; $R_1$ is hydrogen, alkyl, aryl, aryllower-alkyl, naphthyl, furyl, thienyl, pyridinyl or pyrrolyl; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; a stereo, optical or geometrical isomer thereof, or a pharmaceutically acceptable acid addition salts thereof.

2. The compound as defined in claim 1, where n is 2.

3. The compound as defined in claim 2, where $R_1$ is aryl.

4. The compound as defined in claim 3, where X is hydrogen, loweralkyl or trifluoromethyl.

5. The compound as defined in claim 1, which is N-(phenylmethylene)-1,2,3,4-tetrahydro-9-acridinamine.

6. The compound as defined in claim 1, which is N-[(4-fluorophenyl)methylene]-1,2,3,4-tetrahydro-9-acridinamine.

7. The compound as defined in claim 1, which is N-[(3-fluorophenyl)methylene]-1,2,3,4-tetrahydro-9-acridinamine.

8. The compound as defined in claim 1, which is N-[(2-fluorophenyl)methylene-1,2,3,4-tetrahydro-9-acridinamine.

9. The compound as defined in claim 1, which is N-[(2-chlorophenyl)methylene-1,2,3,4-tetrahydro-9-acridinamine.

10. The compound as defined in claim 1, which is N-[(4-chlorophenyl)methylene]-1,2,3,4-tetrahydro-9-acridinamine.

11. The compound as defined in claim 1, which is N-[(2,4-dichlorophenyl)methylene-1,2,3,4-tetrahydro-9-acridinamine.

12. The compound as defined in claim 1, which is N-[(4-methoxyphenyl)methylene]-1,2,3,4-tetrahydro-9-acridinamine.

13. The compound as defined in claim 1, which is N-[(2-methylphenyl)methylene)-1,2,3,4-tetrahydro-9-acridinamine.

14. The compound as defined in claim 1, which is N-[(4-methylphenyl)methylene]-1,2,3,4-tetrahydro-9-acridinamine.

15. The compound as defined in claim 1, which is N-[(4-nitrophenyl)methylene]-1,2,3,4-tetrahydro-9-acridinamine.

16. The compound as defined in claim 1, which is N-[(4-cyanophenyl)methylene]-1,2,3,4-tetrahydro-9-acridinamine.

17. The compound as defined in claim 1, which is N-[(2-hydroxyphenyl)methylene]-1,2,3,4-tetrahydro-9-acridinamine.

18. The compound as defined in claim 1, which is N-[(4-hydroxyphenyl)methylene]-1,2,3,4-tetrahydro-9-acridinamine.

19. The compound as defined in claim 1, which is 1,2,3,4-tetrahydro-N-[(4-trifluoromethylphenyl)methylene]-9-acridinamine.

20. The compound as defined in claim 1, which is N-[(2-thienyl)methylene]-1,2,3,4-tetrahydro-9-acridinamine.

21. The compound as defined in claim 1, which is N-[(2-furyl)methylene]-1,2,3,4-tetrahydro-9-acridinamine.

22. The compound as defined in claim 1, which is N-[(2-pyridinyl)methylene]-1,2,3,4-tetrahydro-9-acridinamine.

23. The compound as defined in claim 1, which is N-[(3-pyridinyl)methylene]-1,2,3,4-tetrahydro-9-acridinamine.

24. The compound as defined in claim 1, which is N-[(4-pyridinyl)methylene]-1,2,3,4-tetrahydro-9-acridinamine.

25. The compound as defined in claim 1, which is 6-chloro-N-(phenylmethylene)-1,2,3,4-tetrahydro-9-acridinamine.

26. The compound as defined in claim 1, which is 7-chloro-N-(phenylmethylene)-1,2,3,4-tetrahydro-9-acridinamine.

27. The compound as defined in claim 1, which is 6-methoxy-N-(phenylmethylene)-1,2,3,4-tetrahydro-9-acridinamine.

28. The compound as defined in claim 1, which is 7-methoxy-N-(phenylmethylene)-1,2,3,4-tetrahydro-9-acridinamine.

29. The compound as defined in claim 1, which is 6-methyl-N-(phenylmethylene)-1,2,3,4-tetrahydro-9-acridinamine.

30. The compound as defined in claim 1, which is 7-methyl-N-(phenylmethylene)-1,2,3,4-tetrahydro-9-acridinamine.

31. The compound as defined in claim 1, which is 6-fluoro-N-(phenylmethylene)-1,2,3,4-tetrahydro-9-acridinamine.

32. The compound as defined in claim 1, which is N-(phenylmethylene)-6-trifluoromethyl-1,2,3,4-tetrahydro-9-acridinamine.

33. The compound as defined in claim 1, which is N-[(1-naphthyl)methylene]-1,2,3,4-tetrahydro-9-acridinamine.

34. The compound as defined in claim 1, which is N-[(2-naphthyl)methylene]-1,2,3,4-tetrahydro-9-acridinamine.

35. The compound as defined in claim 1, which is N-ethylidene-1,2,3,4-tetrahydro-9-acridinamine.

36. The compound as defined in claim 1, which is N-propylidene-1,2,3,4-tetrahydro-9-acridinamine.

37. The compound as defined in claim 1, which is N-(2-methylpropylidene)-1,2,3,4-tetrahydro-9-acridinamine.

38. The compound as defined in claim 1, which is N-butylidene-1,2,3,4-tetrahydro-9-acridinamine.

39. The compound as defined in claim 1, which is N-pentylidene-1,2,3,4-tetrahydro-9-acridinamine.

40. The compound as defined in claim 1, which is N-hexylidene-1,2,3,4-tetrahydro-9-acridinamine.

41. The compound as defined in claim 1, which is N-(4-methylpentylidene)-1,2,3,4-tetrahydro-9-acridinamine.

42. The compound as defined in claim 1, which is N-[(cyclopropyl)methylene]-1,2,3,4-tetrahydro-9-acridinamine.

43. The compound as defined in claim 1, which is N-[(cyclopentyl)methylene]-1,2,3,4-tetrahydro-9-acridinamine.

44. The compound as defined in claim 1, which is N-[(cyclohexyl)methylene]-1,2,3,4-tetrahydro-9-acridinamine.

45. The compound as defined in claim 1, which is N-[(cycloheptyl)methylene]-1,2,3,4-tetrahydro-9-acridinamine.

46. The compound as defined in claim 1, which is N-octylidene-1,2,3,4-tetrahydro-9-acridinamine.

47. The compound as defined in claim 1, which is N-decylidene-1,2,3,4-tetrahydro-9-acridinamine.

48. The compound as defined in claim 1, which is N-dodecylidene-1,2,3,4-tetrahydro-9-acridinamine.

49. The compound as defined in claim 1, which is N-tetradecylidene-1,2,3,4-tetrahydro-9-acridinamine.

50. The compound as defined in claim 1, which is N-hexadecylidene-1,2,3,4-tetrahydro-9-acridinamine.

51. The compound as defined in claim 1, which is N-octadecylidene-1,2,3,4-tetrahydro-9-acridinamine.

52. The compound as defined in claim 1, which is 2,3-dihydro-N-(phenylmethylene)-1H-cyclopenta[b]quinolin-9-amine.

53. The compound as defined in claim 1, which is N-(phenylmethylene)-2,3,4,5-tetrahydro-1H-cyclohepta[b]quinolin-10-amine.

54. A pharmaceutical composition for enhancing the cholinergic function in a mammal which comprises an effective amount of a compound as defined in claim 1 and a carrier therefor.

55. The pharmaceutical composition as defined in claim 50 which comprises N-(phenylmethylene)-1,2,3,4-tetrahydro-9-acridinamine.

56. The pharmaceutical composition as defined in claim 50 which comprises N-[(4-fluorophenyl)methylene]-1,2,3,4-tetrahydro-9-acridinamine.

57. The pharmaceutical composition as defined in claim 50 which comprises N-ethylidene-1,2,3,4-tetrahydro-9-acridinamine.

58. The pharmaceutical composition as defined in claim 50 which comprises N-decylidene-1,2,3,4-tetrahydro-9-acridinamine.

59. The pharmaceutical composition as defined in claim 50 which comprises 2,3-dihydro-N-(phenylmethylene)-1H-cyclopenta[b]-quinolin-9-amine.

60. The pharmaceutical composition as defined in claim 50 which comprises N-(phenylmethylene)-2,3,4,5-tetrahydro-1H-cyclohepta-[b]quinolin-9-amine.

61. A method of enhancing the cholinergic function in a mammal which comprises administering to the mammal an effective cholinergic function enhancing amount of a compound as defined in claim 1.

62. The method as defined in claim 57, which comprises the administration of N-(phenylmethylene)-1,2,3,4-tetrahydro-9-acridinamine.

63. The method as defined in claim 57, which comprises the administration of N-[(4-fluorophenyl)methylene]-1,2,3,4-tetrahydro-9-acridinamine.

64. The method as defined in claim 52, which comprises the administration of N-ethylidene-1,2,3,4-tetrahydro-9-acridinamine.

65. The method as defined in claim 57, which comprises the administration of N-decylidene-1,2,3,4-tetrahydro-9-acridinamine.

66. The method as defined in claim 52, which comprises the administration of 2,3-dihydro-N-(phenylmethylene)-1H-cyclopenta[b]quinolin-9-amine.

67. The method as defined in claim 57, which comprises the administration of N-(phenylmethylene)-2,3,4,5-tetrahydro-1H-cyclohepta[b]quinolin-9-amine.

* * * * *